(12) United States Patent
Maziewski (10) Patent No.: US 12,230,274 B2
(45) Date of Patent: Feb. 18, 2025

(54) SPEECH RECOGNITION WITH BRAIN-COMPUTER INTERFACES

(71) Applicant: Intel Corporation, Santa Clara, CA (US)

(72) Inventor: Przemyslaw Maziewski, Gdansk (PL)

(73) Assignee: Intel Corporation, Santa Clara, CA (US)

( * ) Notice: Subject to any disclaimer, the term of this patent is extended or adjusted under 35 U.S.C. 154(b) by 916 days.

(21) Appl. No.: 17/121,444

(22) Filed: Dec. 14, 2020

(65) Prior Publication Data

US 2021/0104244 A1    Apr. 8, 2021

(51) Int. Cl.
| | | |
|---|---|---|
| *G10L 15/00* | (2013.01) |
| *G10L 15/06* | (2013.01) |
| *G10L 15/24* | (2013.01) |
| *G10L 15/26* | (2006.01) |
| *H04R 1/46* | (2006.01) |

(52) U.S. Cl.
CPC ............ *G10L 15/26* (2013.01); *G10L 15/063* (2013.01); *G10L 15/24* (2013.01); *H04R 1/46* (2013.01)

(58) Field of Classification Search
USPC ..................... 704/1–275; 706/1–62, 900–903
See application file for complete search history.

(56) References Cited

U.S. PATENT DOCUMENTS

| | | | |
|---|---|---|---|
| 10,795,440 B1 | 10/2020 | Chevillet et al. | |
| 10,893,356 B2 * | 1/2021 | Lawrenson | .......... H04R 1/1083 |
| 2007/0100630 A1 | 5/2007 | Manabe et al. | |
| 2017/0172493 A1 * | 6/2017 | Rahman | ............... A61B 5/6801 |
| 2019/0179604 A1 | 6/2019 | Alexander et al. | |
| 2019/0333505 A1 * | 10/2019 | Stavisky | ................ A61B 5/741 |
| 2021/0267539 A1 * | 9/2021 | Grant | ..................... A61B 5/369 |

FOREIGN PATENT DOCUMENTS

KR    102074794 B1    2/2020

OTHER PUBLICATIONS

Sparks Lindsay; Collaborative Human Edge Node Devices and Related Systems and Methods; 2019 (Year: 2019).*
EP Search Report for EP App. No. 21197734.3 Mailed Mar. 17, 2022, 8 Pages.

(Continued)

*Primary Examiner* — Marcellus J Augustin
(74) *Attorney, Agent, or Firm* — Fletcher Yoder, P.C.

(57) ABSTRACT

In an embodiment, a system includes a first sensor sensing brain signal data from a user, the brain signal data including nerve signals transmitted via a brain of the user and corresponding to a first set of words spoken by the user. The system also includes a second sensor sensing audio data from the user corresponding to the first set of words and one or more processors communicatively coupled to the first sensor and the second sensor. In the embodiment, the one or more processors generate text data based on the audio data using a machine learning algorithm and re-train the machine learning algorithm based on the brain signal data and the text data to generate a re-trained machine learning algorithm, wherein the re-trained machine learning algorithm generates second text data associated with a second set of words based on second brain signal data.

20 Claims, 6 Drawing Sheets

(56) References Cited

OTHER PUBLICATIONS

Devi et al. "Hybrid Brain Computer Interface in Wheelchair Using Voice Recognition Sensors," 2014 International Conference on Computer Communication and Informatics (ICCCI -2014), Jan. 3-5, 2014, Coimbatore, India.

Bocquelet et al. "Key considerations in designing a speech brain-computer interface," 2016 Journal of Physiology-Paris, vol. 110, Issue 4, Part A, pp. 392-341, ISSN 0928-4257.

"Researchers Translate Brain Signals Directly Into Speech." Healthinnovations- Latest Innovative Health & Medical News Jan. 30, 2019, last accessed Dec. 14, 2020; https://health-innovations.org/2019/01/30/researchers-translate-brain-signals-directly-into-speech/ last accessed Dec. 14, 2020.

"MindWave Mobile 2 Brainwave Sensing Headset," NeuroSky 2018, last accessed Dec. 14, 2020; https://store.neurosky.com/pages/mindwave.

Sugawara T. et al. "Laser-Based Audio Injection on Voice-Controllable Systems," last accessed Dec. 18, 2020; https://lightcommands.com/ Last Accessed Dec. 18, 2020.

Roy et al. "Inaudible Voice Commands: The Long-Range Attack and Defense," University of Illinois at Urbana-Champaign 2018.

\* cited by examiner

SPEECH RECOGNITION WITH BRAIN-COMPUTER INTERFACES

BACKGROUND

The present disclosure relates generally to non-auditory speech recognition and, more particularly, transforming brain signal data into text data.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Audio-based speech recognition (ASR) techniques receive audio data (e.g., spoken words) as input, process and transform the audio data into text data, and generate transcriptions of spoken words. Internet of Things (IoT) and smart devices use ASR to process spoken commands by a user and carry out accompanying tasks. However, attempting to use ASR in public places can expose private information (e.g., health information, financial information, personal information, business information, confidential information, and so forth) to unintended parties and/or may introduce inaccuracies resulting from background noise.

BRIEF DESCRIPTION OF THE DRAWINGS

Various aspects of this disclosure may be better understood upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Microphones or other audio sensors may record spoken audio data from a user for processing using ASR techniques. Usage of ASR techniques in public places may expose sensitive information (e.g., health information, financial information, business information, personal information, confidential information, and so forth) to unintended recipients (e.g., that may overhear the information) and may potentially result in financial losses, identity theft, and/or any other number of adverse issues. Additionally or alternatively, a user of ASR techniques may not want to disturb other people in a surrounding area, such as a home, office, or public place. Brain-computer interfaces (BCIs) may communicatively couple a brain of a user to a computing device, such as a tablet, laptop, mobile device, smart phone, headset, wearable device, server, or any other suitable computing device. BCIs may sense and/or measure brain signals (e.g., electrical activity) while a user performs certain actions or tasks, such as speaking. As brain signals are non-auditory, the issues associated with usage of ASR techniques (e.g., as described above) may be mitigated by non-auditory speech recognition based on brain signals.

Figure 1:
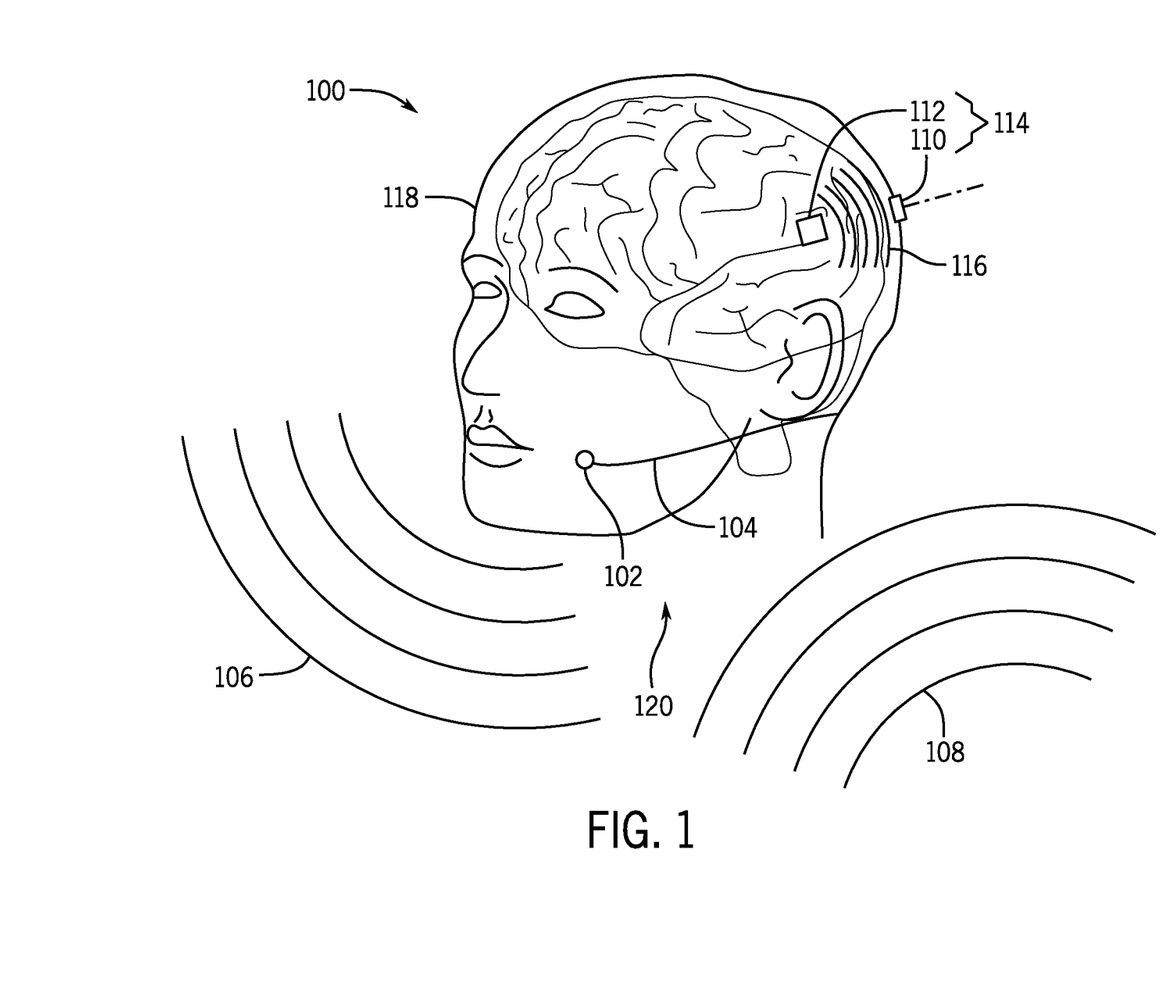
FIG. 1 is a diagram of a device incorporating a non-auditory speech recognition system, in accordance with an embodiment of the present disclosure.

With the preceding in mind, FIG. 1 is a diagram of a device 120 incorporating a non-auditory speech recognition system 100 having a first sensor 102 and a second sensor 112, in accordance with an embodiment of the present disclosure. In some embodiments, the device 120 may be a wearable device having any number of sensors for sensing audio data and/or brain signal data and a frame 104 for supporting the sensors. For example, the wearable device may be worn on a part of a user 118, such as on a head and/or a neck of the user 118. In certain embodiments, the first sensor 102 may sense speech 106 from the user 118 and/or speech 108 heard by the user 118. The first sensor 102 may be an audio sensor (e.g., microphone), biometric sensor, vibration sensor, bone conduction sensor, and/or accelerometer, and the first sensor 102 may sense audio data (e.g., spoken voice), biometric signals (e.g., electromyography (EMG) signals), and/or vibrations from the user 118. In some embodiments, the first sensor 102 may be any type of microphone, such as a condenser microphone, a contact microphone, and/or a dynamic microphone. For example, the first sensor 102 may be a condenser microphone and may include a component (e.g., diaphragm) that vibrates due to sound waves (e.g., spoken voice) from the user 118. Additionally or alternatively, the first sensor 102 may be a contact microphone and may contact the user 118 during a sensing period. For example, the first sensor 102 may be a piezoelectric microphone and may sense vibrations from the user 118 and convert vibrations into audio data (e.g., electrical signals). In certain embodiments, the first sensor 102 may be a dynamic microphone and may include an induction component (e.g., a coil of wire) attached to a diaphragm and positioned in a magnetic field, such as the magnetic field of a permanent magnet. Sound waves from the user 118 may vibrate and move the diaphragm and the induction component with it. Movement of the induction component may produce a current in the induction component through electromagnetic induction due to the presence of the magnetic field and thus convert the sound waves into audio data (e.g., current).

Additionally or alternatively, the first sensor 102 may be a vibration sensor. For example, the first sensor 102 may sense a vibration in a nasal bone of the user 118. More specifically, the first sensor 102 may be an electrode that measures an electrical potential difference in the user 118 (e.g., at a body part of the user 118, such as a head and/or neck) and generates signal data for transmission to and processing by one or more components of the non-auditory speech recognition system 100. In some embodiments, the first sensor 102 may include one or more vibration sensors without including a microphone, as the microphone may capture unwanted and/or ambient noise that may affect accuracy of the captured vibrations.

In some embodiments, the first sensor 102 may be a piezoelectric sensor and may measure vibrations due to movement of a body part of the user 118 (e.g., head and/or neck) during contact with the user 118. Additionally or alternatively, the first sensor 102 may include an optical device, such as a camera, a laser Doppler vibrometer, and/or a light detection and ranging (LIDAR) system, and may measure vibrations on a surface (e.g., a body part of the user 118) without contacting the surface. For example, the first sensor 102 may emit light (e.g., a laser beam) towards a body part of the user 118 and may sense reflected light from the body part. As such, the first sensor 102 may determine vibration amplitude and vibration frequency based on the Doppler shift between the emitted light and the reflected light. Data (e.g., vibration data, audio data, light data) detected by the first sensor 102 may include desired signal components, as well as noise (e.g., unwanted) components. Signal to noise ratio is a comparison between a level of the desired signal and a level of noise. Different locations on a user, such as user 118, may provide better measurements for certain types of sensors (e.g., vibration sensors, microphones,) over other types of sensors. For example, an audio sensor may provide a better signal to noise ratio (SNR) for audio data near a mouth than near an ear of the user 118, and a bone conduction sensor may provide a better SNR when placed near a nasal bone than near a cheek of the user 118. As such, one or more sensors may be selectively placed at different locations on the user 118 to ensure accuracy of the sensed vibrations and/or audio for increased SNR. In order to accommodate placing sensors at different locations on the user 118, the device 120 may include a headset device, headphones, a headband, earphones, scarf, or any other suitable wearable device or combination of wearable devices.

As used herein, "brain-computer interface" may refer to a device or system that provides a communication pathway between a brain and any number of external devices such that brain signals may communicate with (e.g., send and/or receive information to and from) and/or control the external device(s). The device may also include a brain-computer interface 114 including a second sensor 112 and processing circuitry, such as processor 110. The processor 110 may include receiving and conversion circuitry for receiving audio data from the first sensor 102 and/or brain signal data from the second sensor 112. The brain-computer interface 114 may measure brain activity from user 118, may extract features associated with the brain activity, and may generate and/or transmit brain signal data 116 associated with the brain activity and/or the extracted features. For example, the second sensor 112 may include any number of electrodes disposed on a scalp and/or a brain of the user 118 and the second sensor 112 may detect electrical signals from the brain of the user 118. The second sensor 112 may sense electrical activity (e.g., electroencephalography (EEG), electrocorticography (ECoG)) and may measure voltage fluctuations resulting from current within neurons of the brain of the user 118.

In certain embodiments, the second sensor 112 may sense electrical activity concurrently with (e.g., at approximately the same time and/or for the same duration as) the first sensor 102 sensing audio data. For example, the first sensor 102 may sense audio data corresponding to speech 106 from user 118 or speech 108 from another individual that is heard by the user 118, and the second sensor 112 may sense brain signal data 116 corresponding to the speech 106 from the user 118 or the speech 108 from another individual that is heard by the user 118. As such, the non-auditory speech recognition system 100 may sense and/or may generate audio data and brain signal data corresponding to a set of words spoken by the user 118 or heard by user 118. Additionally or alternatively, the second sensor 112 may measure blood flow and/or changes in blood flow (e.g., function magnetic resonance imaging (fMRI)) in the brain of the user 118 and may generate the brain signal data 116 based on the measured blood flow.

As used herein, "auditory speech recognition" may refer to receiving audio data corresponding to spoken words and processing the audio data to generate text data corresponding to the spoken words (e.g., via a machine learning algorithm). "Non-auditory speech recognition" may refer to receiving data in a format different from audio data (e.g., brain signal data) corresponding to spoken and/or heard words and processing the data to generate text data corresponding to the spoken and/or heard words (e.g., via a machine learning algorithm). In some embodiments, the non-auditory speech recognition system 100 may re-train a machine learning algorithm based on audio data from the first sensor 102 and brain signal data 116 from the second sensor 112. In certain embodiments, the machine learning algorithm may be initially trained according to an auditory speech recognition process. For example, a user, such as user 118 in FIG. 1, another user, or any number of users, may read aloud a passage of text and the machine learning algorithm may be trained based on recordings of the user's speech and the corresponding passage of text. As such, audio data generated from the user's speech may be input into the machine learning algorithm and the machine learning algorithm may identify spoken words in the audio data and output text data corresponding to the spoken words. Additionally or alternatively, the user may read aloud a set of words that correspond to commands recognized by a computing device and the machine learning algorithm may be trained based on recordings of the spoken words and the commands. In certain embodiments, the commands may cause the computing device to perform an associated function. For example, the user may say "turn on" to activate the computing device. Accordingly, the machine learning algorithm may associate spoken words with the corresponding text data, and identify subsequent spoken words based on these associations.

Once the machine learning algorithm has been trained according to the auditory speech recognition process, the non-auditory speech recognition system 100 may re-train the machine learning algorithm to identify and output text data based on brain signal data 116. For example, the non-auditory speech recognition system 100 may receive audio data and brain signal data corresponding to the same spoken and/or overheard speech. The non-auditory speech recognition system 100 may re-train the machine learning algorithm to identify features of the brain signal data corresponding to the spoken and/or overheard words.

Figure 2:
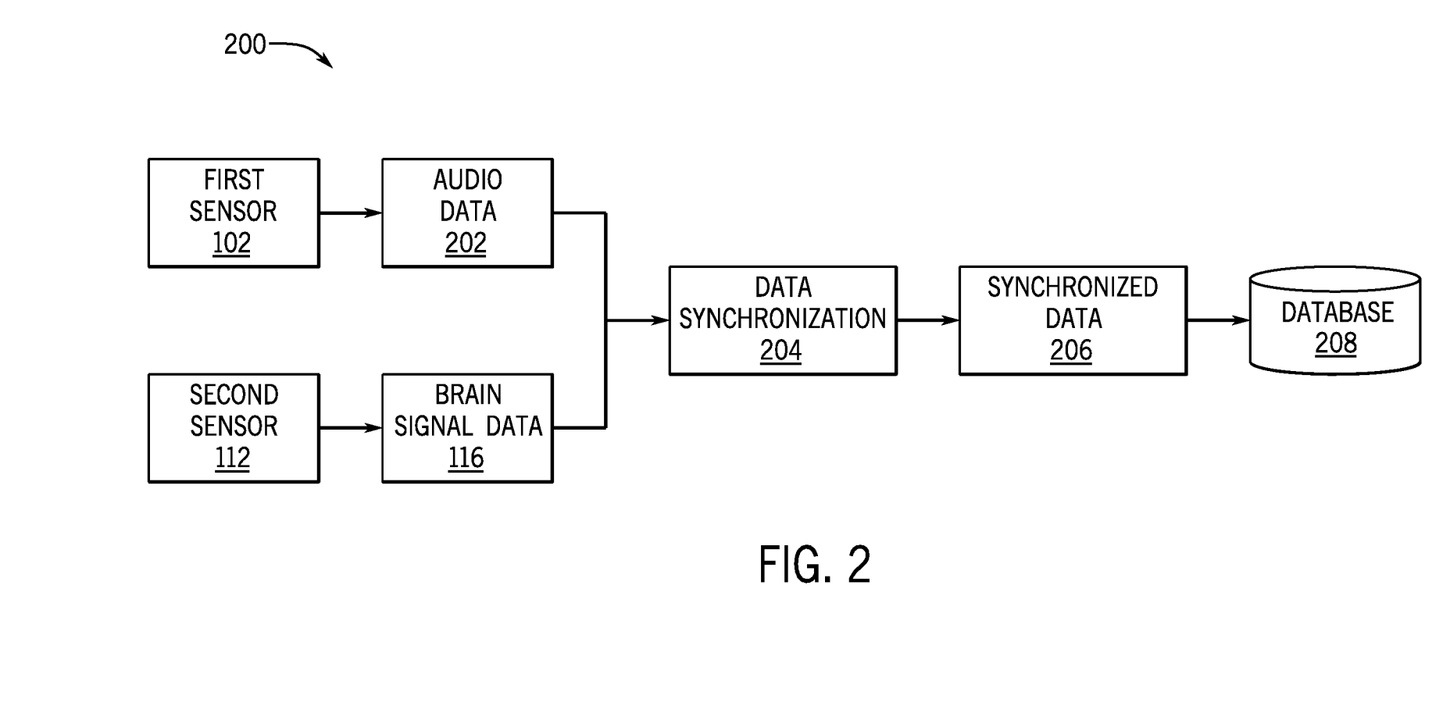
FIG. 2 is a block diagram illustrating data flow when generating synchronized data, in accordance with an embodiment of the present disclosure.

With the preceding in mind, FIG. 2 is a block diagram illustrating data flow 200 when generating synchronized data 206, in accordance with an embodiment of the present disclosure. An audio sensor, such as the first sensor 102 in FIG. 1, may generate and/or receive audio data 202 from a user 118. For example, the first sensor 102 may generate audio data 202 corresponding to speech from the user 118 and/or speech overheard by the user 118. In certain embodiments, the first sensor 102 may receive the audio data 202 during a sensing period based on a threshold time duration (e.g., one minute, five minutes, ten minutes, and so forth). For example, the non-auditory speech recognition system 100 may transmit a control signal to the first sensor 102 to begin and/or end the sensing period based on the threshold time duration. Additionally or alternatively, the non-auditory speech recognition system 100 may include a user interface and may display an indication to the user 118 to begin and/or end speaking based on the threshold time duration. In some embodiments, the user interface may display a particular passage of text for the user 118 to read aloud during the sensing period. Alternatively, the user interface may indicate the user may speak freely (e.g., randomly) during the sensing period.

A brain signal sensor, such as the second sensor 112 in FIG. 1, may generate and/or receive brain signal data 116 from the user 118. In some embodiments, the second sensor 112 may generate brain signal data 116 corresponding to brain activity while the user 118 speaks and/or while the user 118 hears speech from another user. For example, the second sensor 112 may measure electrical activity from a brain of the user 118 during a sensing period that corresponds to the first sensor 102 sensing the audio data 202. In certain embodiments, the non-auditory speech recognition system 100 may generate and/or transmit control signals to the first sensor 102 and/or the second sensor 112 to begin and/or end the sensing period. For example, the first sensor 102 may generate and/or transmit an audio signal to processing circuitry, such as processor 110 in FIG. 1, of the non-auditory speech recognition system 100 in response to detecting audio stimuli. The non-auditory speech recognition system 100 may receive the audio signal from the first sensor 102 and may generate a control signal in response to the audio signal. In certain embodiments, the non-auditory speech recognition system 100 may transmit the control signal to the second sensor 112 and the second sensor 112 may begin a sensing period in response to receiving the control signal. Additionally or alternatively, the non-auditory speech recognition system 100 may generate and/or transmit a control signal to operate (e.g., begin a sensing period) the first sensor 102 in response to receiving a brain signal corresponding to electrical activity at a brain of the user 118 from the second sensor 112.

In some embodiments, the audio data 202 may include metadata, such as a time duration associated with the audio data 202 and any number of time stamps (e.g., beginning time stamp, ending time stamp) associated with the audio data 202. For example, the first sensor 102 may generate metadata (e.g., time stamp, time duration) associated with the audio data 202 and may transmit the metadata to processing circuitry 110 of the non-auditory speech recognition system 100. The non-auditory speech recognition system 100 may analyze the time duration and/or the time stamps and may determine when the audio data 202 was sensed and/or generated by the first sensor 102, a beginning of the sensing period for the first sensor 102, an ending of the sensing period for the first sensor 102, a total time duration the first sensor 102 sensed and/or generated the audio data 202, and the like.

In certain embodiments, the brain signal data 116 may include metadata, such as a time duration associated with the brain signal data 116 and any number of time stamps (e.g., beginning time stamp, ending time stamp) associated with the brain signal data 116. For example, the second sensor 112 may generate metadata (e.g., time stamp, time duration) associated with the brain signal data 116 and may transmit the metadata to processing circuitry of the non-auditory speech recognition system 100, such as processor 110 of the brain-computer interface 114. The non-auditory speech recognition system 100 may analyze the time duration and/or the time stamps and may determine when the brain signal data 116 was sensed and/or generated by the second sensor 112, a beginning of a sensing period for the second sensor 112, an ending of the sensing period for the second sensor 112, a total time duration the second sensor 112 sensed and/or generated the brain signal data 116, and the like.

In certain embodiments, the non-auditory speech recognition system 100 may perform data synchronization 204 on the audio data 202 and the brain signal data 116 to generate synchronized data 206. In particular, the non-auditory speech recognition system 100 may align the audio data 202 and the brain signal data 116 such that the speech recorded by the first sensor 102 corresponds to the electrical activity sensed by the second sensor 112 (e.g., concurrently with, at a same time) to generate the synchronized data 206. For example, the non-auditory speech recognition system 100 may determine a sensing period associated with the audio data 202 began five seconds before a sensing period associated with the brain signal data 116, and may time-synchronize the audio data 202 and the brain signal data 116 by aligning a beginning time stamp associated with the brain signal data 116 five seconds after the beginning time stamp associated with the audio data 202.

In some embodiments, the non-auditory speech recognition system 100 may synchronize the audio data 202 and the brain signal data 116 with a time delay (e.g., less than a second, less than 800 milliseconds, less than 500 milliseconds, less than 300 milliseconds). For example, the brain of a user 118 may take a short time to process heard speech or to generate speech such that electrical activity associated with the brain processing one or more heard words may lag behind audio data corresponding to the words recorded by the first sensor 102. Additionally or alternatively, the brain of a user 118 may process and generate electrical activity to begin speaking before audio data is recorded, thus requiring a time delay for the brain signal data 116. As such, the non-auditory speech recognition system 100 may generate a time delay to ensure the electrical activity (e.g., brain signal data 116) associated with words spoken by the user 118 or heard by the user 118 aligns with the speech (e.g., audio data) recorded by the first sensor 102. In some embodiments, the time delay may be a uniform time delay for any user of the non-auditory speech recognition system 100. Additionally or alternatively, the non-auditory speech recognition system 100 may determine a time delay for each user and the time delays may differ from user to user. In certain embodiments, the non-auditory speech recognition system 100 may store the synchronized data 206, the audio data 202, and/or the brain signal data 116 in a storage device associated with the non-auditory speech recognition system 100, such as database 208. Additionally or alternatively, the non-auditory speech recognition system 100 may transmit the synchronized data 206, the audio data 202, and/or the brain signal data 116 to a remote storage device.

Figure 3:
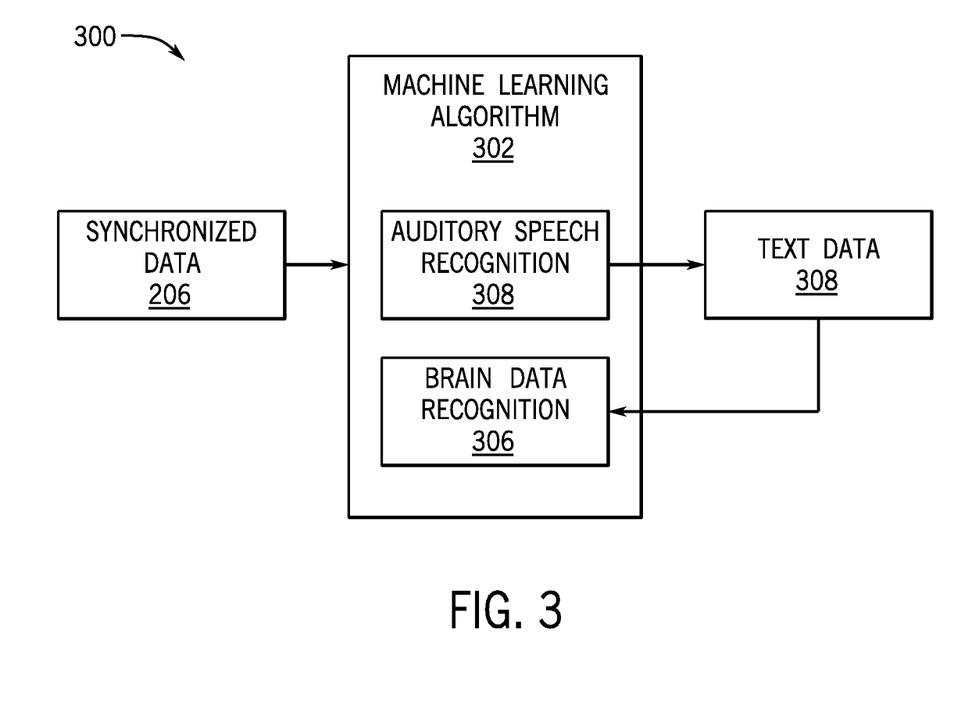
FIG. 3 is a block diagram illustrating data flow when training a machine learning algorithm using the synchronized data of FIG. 2, in accordance with an embodiment of the present disclosure.

After generating the synchronized data 206, the non-auditory speech recognition system 100 may re-train an auditory speech recognition machine learning algorithm to receive only non-auditory, brain signal data and thus generate text data corresponding to and/or based on the brain signal data. With the preceding in mind, FIG. 3 is a block diagram illustrating data flow 300 when training a machine learning algorithm to output text data based on synchronized data 206 and brain signal data 116. In certain embodiments, the non-auditory speech recognition system 100 may include a machine learning algorithm 302 and processing circuitry, such as the processor 110, which may perform the machine learning algorithm 302. For example, the machine learning algorithm 302 may include an auditory speech recognition component 304 that generates text data 308 based on input audio data, such as audio data 202 in FIG. 2. In certain embodiments, the auditory speech recognition component 304 may extract features (e.g., frequency, amplitude) from the audio data, may perform data processing steps (e.g., analog/digital conversion, Fourier transform, separating the audio data into any number of frames) on the audio data, and may generate waveforms (e.g., vibration waveforms, audio waveforms), spectrograms, and/or any other suitable signal format based on the audio data. For example, the auditory speech recognition component 304 may compare features of the audio data with expected features from stored audio samples. The auditory speech recognition component 304 may generate the text data 308 based on these comparisons.

In certain embodiments, the non-auditory speech recognition system 100 may include any number of sensors (e.g., camera, biometric sensor, audio sensor, accelerometer, brain signal sensor, and so forth), and each sensor may transmit audio data and/or brain signal data, or data associated with the audio data and/or brain signal data, to the processor 110. For example, a camera may generate signal data associated with neck and/or facial muscle movements of a user 118, and a brain signal sensor may generate brain signal data associated with electrical activity in the brain of the user 118. The sensors may transmit respective signal data to the processor 110, and the processor 110 may combine the signal data into the synchronized data 206.

After generating the text data 308, the non-auditory speech recognition system 100 may utilize the text data 308 and the synchronized data 206 to re-train the machine learning algorithm 302. For example, the text data 308 may include a string of text (e.g., words, phrases) associated with the synchronized data 206. The machine learning algorithm 302 may include a brain data recognition component 306 that learns to generate text data based on input brain signal data, such as brain signal data 116 in FIG. 1. The non-auditory speech recognition system 100 may utilize the brain signal data and the output text data 308 to re-train the machine learning algorithm 302. For example, the brain data recognition component 306 may extract features (e.g., frequency, amplitude) from the brain signal data, may perform data processing steps (e.g., analog/digital conversion, Fourier transform, separating the brain signal data into any number of frames) on the brain signal data, and may generate waveforms (e.g., brain signal waveforms), spectrograms, and/or any other suitable signal format based on the brain signal data. The brain data recognition component 306 may associate the text data 308 with the brain signal data. In some embodiments, the brain data recognition component 306 may generate expected features based on the training brain signal data and the text data 308. For example, the expected features may be compared with extracted features from input brain signal data, and associated with the text data 308. As such, the non-auditory speech recognition system 100 may store sample brain signal data and associated text data, and use these associations to identify text data corresponding to subsequent brain signal data.

Additionally, the non-auditory speech recognition system 100 may generate a profile associated with the user 118 during and/or after re-training the machine learning algorithm 302. The user profile may include brain signal characteristics (e.g., frequencies, amplitudes, changes in frequencies, changes in amplitudes, voltages, currents) associated with the user. Additionally or alternatively, the user profile may include the audio data 202, the brain signal data 116, text data 308, corresponding time delay, and extracted features associated with the audio data 202 and the brain signal data 116. In certain embodiments, the non-auditory speech recognition system 100 may store the user profile, the audio data 202, and the brain signal data 116 in a storage device associated with the non-auditory speech recognition system 100. As such, the non-auditory speech recognition system 100 may retrieve the corresponding user profile to generate text data corresponding to subsequent brain signal data sensed from the user 118.

Figure 4:
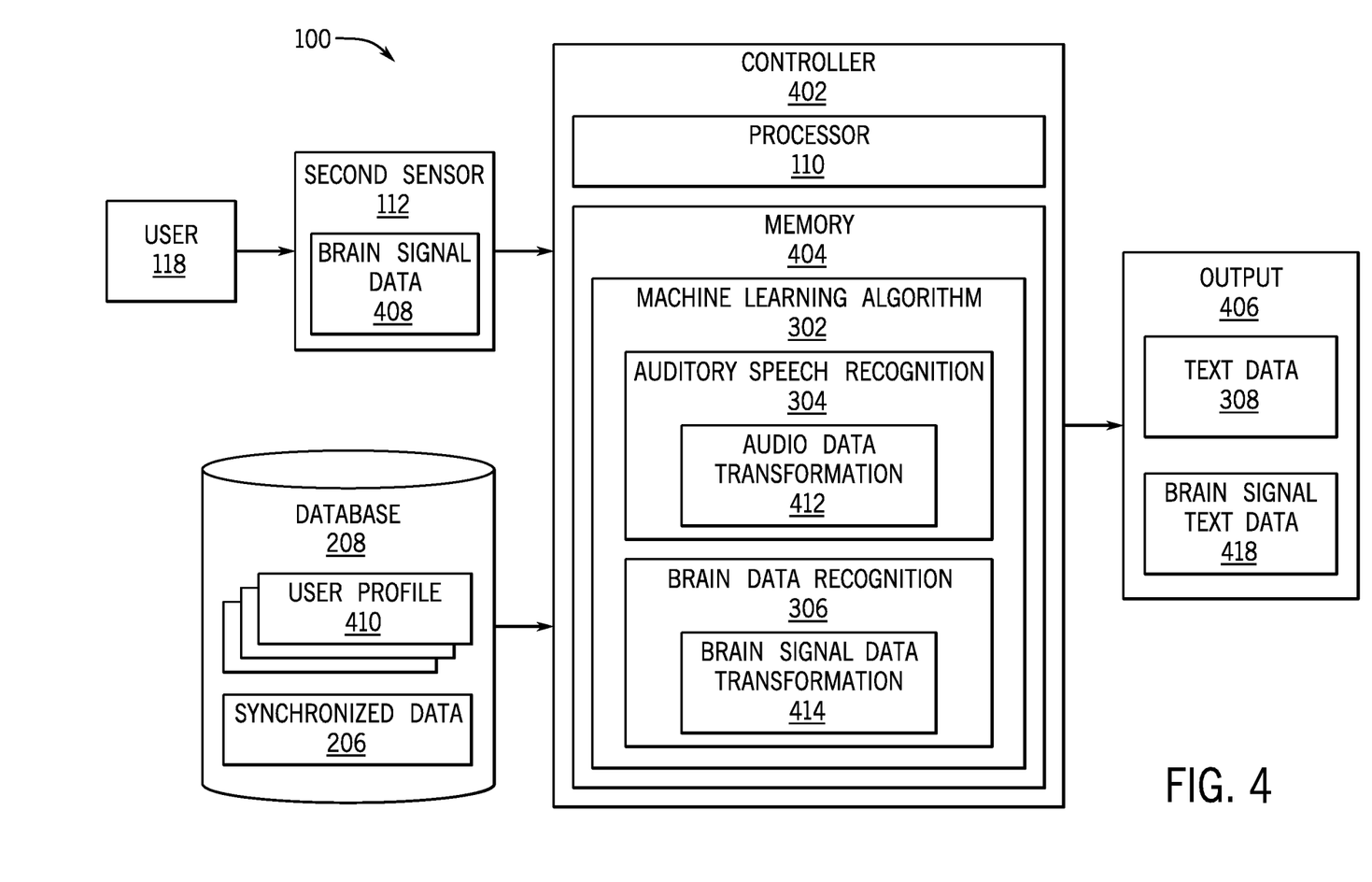
FIG. 4 is a block diagram of the non-auditory speech recognition system of FIG. 1, in accordance with an embodiment of the present disclosure.

After re-training the machine learning algorithm 302, the non-auditory speech recognition system 100 may receive input brain signal data 116 and may use the machine learning algorithm 302 to generate text data from the brain signal data 116 (e.g., after the machine learning algorithm 302 has completed re-training and been implemented as part of the non-auditory speech recognition system 100). That is, the machine learning algorithm 302 may generate the text data based on the brain signal data 116, without the audio data 202. With the preceding in mind, FIG. 4 illustrates a block diagram of the non-auditory speech recognition system 100 of FIG. 1 generating brain signal text data 418 utilizing the machine learning algorithm 302 of FIG. 3 based on input brain signal data 408 without the use of audio data, in accordance with an embodiment of the present disclosure. The non-auditory speech recognition system 100 may generate text data 308 using audio data 202 and may re-train the machine learning algorithm 302 by correlating brain signal data 116 with the text data 308. As such, the re-trained machine learning algorithm 302 may generate brain signal text data 418 based on input brain signal data 408 without the use of audio data. For example, a brain signal sensor, such as second sensor 112, may record electrical activity associated with a brain of the user 118 and generate input brain signal data 408. In some embodiments, the non-auditory speech recognition system 100 may include a database 208 that may store synchronized data 206. In certain embodiments, the synchronized data 206 may include a recording (e.g., audio data 202) of speech associated with a user, such as user 118, and brain signal data 116 (e.g., electrical activity associated with the brain of the user 118 hearing, generating, and/or processing speech) associated with the user 118. Additionally, the database 208 may store a set of user profiles, such as user profile 410 associated with the user 118, and the user profile 410 may be associated with a subset of the synchronized data 206.

A brain signal sensor, such as second sensor 112 in FIG. 1, may receive input brain signal data 408 from a user 118 and the non-auditory speech recognition system 100 may perform brain signal transformation 414 to extract features (e.g., frequency, amplitude), perform data processing steps (e.g., analog/digital conversion, Fourier transform, separating the brain signal data 408 into any number of frames), and generate waveforms (e.g., brain signal waveforms), spectrograms, and/or any other suitable signal format based on the input brain signal data 408. For example, a brain signal sensor may generate brain signal data associated with electrical activity of a brain of the user 118. The sensor may transmit brain signal data 408 to a processor, such as processor 110 in FIG. 1.

In certain embodiments, the non-auditory speech recognition system 100 may include a controller 402, which may be provided as part of a computing device, such as a personal computer, a laptop, a tablet, a mobile device, a wearable device, a server, or any other suitable computing device, and the controller 402 may communicatively couple to the computing device via a wireless, optical, coaxial, wired, or other suitable connection. As such, the controller 402 may include one or more processors, such as processor 110, (collectively referred to herein as "a processor 110"), which may be provided in the form of one or more general purpose microprocessors, one or more application specific integrated circuits (ASICs), one or more field programmable logic arrays (FPGAs), and the like. The processor 110 may be communicatively coupled to the database 208 and one or more sensors, such as first sensor 102 in FIG. 1 and second sensor 112. The controller 402 may be coupled to the sensors 102, 112 and the database 208 by any suitable techniques for communicating signal data and control signals between the controller 402, the database 208, and the sensors 102, 112, such as a wireless, optical, coaxial, wired, or other suitable connection. In some embodiments, the controller 402 may include receiving and conversion circuitry for receiving synchronized data for training a machine learning algorithm, and for receiving and transforming input brain signal data 408 to generate brain signal text data 418.

In certain embodiments, the processor 110 may perform a machine learning algorithm, such as the machine learning algorithm 302, which may include instructions that synchronize the audio data 202 and the brain signal data 116, and generate text data 308, as previously discussed. For example, the machine learning algorithm 302 may include the auditory speech recognition component 304. The auditory speech recognition component 304 may receive the synchronized data 206 and may perform audio data transformation 412 and may extract features (e.g., frequency, amplitude) from the synchronized data 206, may perform data processing steps (e.g., analog/digital conversion, Fourier transform, separating the synchronized data 206 into any number of frames) on the synchronized data 206, and may generate waveforms (e.g., vibration waveforms, audio waveforms), spectrograms, and/or any other suitable signal format based on the synchronized data 206. In some embodiments, the non-auditory speech recognition system 100 may include stored audio samples associated with words and/or phrases, such as text data 308 and the non-auditory speech recognition system 100 may compare the audio data 202 to stored audio samples to identify spoken words and/or phrases in the audio data 202 based on the comparison. For example, the audio data transformation 412 may compare features of the audio data with expected features from stored audio samples. As such, the non-auditory speech recognition system 100 may generate output 406 (e.g., text data 308) based on these comparisons. The machine learning algorithm 302 may input synchronized data 206 and the extracted features, and the processor 110 may train the machine learning algorithm 302. In certain embodiments, the machine learning algorithm may generate a user profile 410 based on the synchronized data 206 and the text data 308. For example, the user profile 410 may be retrieved by the machine learning algorithm 302, and the machine learning algorithm 302 may utilize the user profile 410 to generate brain signal text data 418 from input brain signal data 408. In certain embodiments, the machine learning algorithm may access expected waveforms corresponding to brain signal data of the user 118.

In some embodiments, the memory 404 may include instructions that re-train the machine learning algorithm 302, receive the input brain signal data 408, and generate the brain signal text data 418 based on the input brain signal data 408. The machine learning algorithm 302 may include brain signal data transformation 414 and may perform data processing steps on input brain signal data 408. In certain embodiments, the brain signal data transformation 414 may include instructions executable by the processor 110 to perform feature extraction, perform data cleanup, associate and/or combine input data sets, and/or normalize data to provide an input dataset for the machine learning algorithm 302. In some embodiments, the non-auditory speech recognition system 100 may perform a data cleanup process to resolve data inconsistencies, remove noisy data points, and/or remove outlier data points in the input brain signal data 408. For example, the non-auditory speech recognition system 100 may remove data points from the input brain signal data 408 that fall outside a specified or threshold range, such as one standard deviation, two standard deviations, or more, from an average data point.

In certain embodiments, the non-auditory speech recognition system 100 may perform a data separation process to separate the input brain signal data 408 into any number of frames and may perform an analog/digital conversion process to convert the input brain signal data 408 into a digital signal. Additionally or alternatively, the non-auditory speech recognition system 100 may perform a Fourier transform on the input brain signal data 408 to generate a first set of frequencies associated with the audio data 202 and a second set of frequencies associated with the brain signal data 408.

In certain embodiments, the non-auditory speech recognition system 100 may extract features (e.g., frequencies, amplitudes, and so forth) associated with the input brain signal data 408. The machine learning algorithm 302 may identify and extract features from the input brain signal data 408, such as amplitude of vibrations, frequency of vibrations, changes in vibration direction (e.g., angular direction, rotational direction), and the like. Additionally, the brain data recognition component 306 may include instructions that cause the processor 110 to generate waveforms based on extracted features from the brain signal data 408 and may compare the generated waveforms to expected waveforms associated with synchronized data 206. For example, the non-auditory speech recognition system 100 may associate previously received brain signal data (e.g., brain signal data 116) with text data 308 generated based on audio data 202 sensed concurrently with the brain signal data. The non-auditory speech recognition system 100 may generate expected waveforms associated with the brain signal data 114 to identify words and/or phrases based on subsequent brain signal data (e.g., input brain signal data 408) As such, the machine learning algorithm 302 may compare received brain signal data to the expected waveforms and may determine brain signal text data 418 heard by the user 118 and/or processed by the brain of the user 118.

In certain embodiments, the processor 110 may generate the brain signal text data 418 utilizing the machine learning algorithm 302. For example, the second sensor 112 may sense the brain signal data 408 (e.g., electrical activity) and may transmit the brain signal data 408 to the controller 402.

The brain signal data 408 may include electrical activity associated with a brain of the user 118, such as voltage amplitudes, voltage frequencies, changes in voltage, and the like. Additionally or alternatively, the brain signal data 408 may correspond to any number of words heard by the user 118 and/or processed by the brain of the user 118 (e.g., when a user thinks of words or phrases to be spoken).

The processor 110 may input the brain signal data 408 into the machine learning algorithm 302, and the brain data recognition component 306 may receive the brain signal data 408 and generate output 406 (e.g., brain signal text data 418) based on the brain signal data 408. For example, the brain data recognition component 306 may extract features of the brain signal data 408 and may compare the extracted features to expected features associated with training data (e.g., synchronized data 206) and/or extracted features associated with training data based on electrical activity sensed at a brain of the user 118. As such, the machine learning algorithm 302 may compare waveforms associated with the brain signal data 408 with expected waveforms corresponding to words and/or phrases and may determine a set of words and/or sounds associated with the brain signal data 408 based on any number of matches during the comparison. In certain embodiments, the brain signal text data 418 may correspond to the same words processed by the brain of the user 118 in the brain signal data 408 (e.g., words heard by the user 118 and processed by the brain of the user 118 and/or words processed by the user 118 and to be spoken by the user 118). In certain embodiments, the non-auditory speech recognition system 100 may transmit the generated brain signal text data 418 to any number of computing devices.

In some embodiments, the machine learning algorithm 302 may be implemented as software stored in a memory 404 and/or any number of storage devices of the non-auditory speech recognition system 100. In some embodiments, the memory 404 may include one or more tangible, non-transitory computer-readable media that store instructions executable by the processor 110 and/or data to be processed by the processor 110. For example, the memory 404 may include random access memory (RAM), read only memory (ROM), rewritable non-volatile memory, such as flash memory, hard drives, optical discs, and/or the like.

Figure 5:
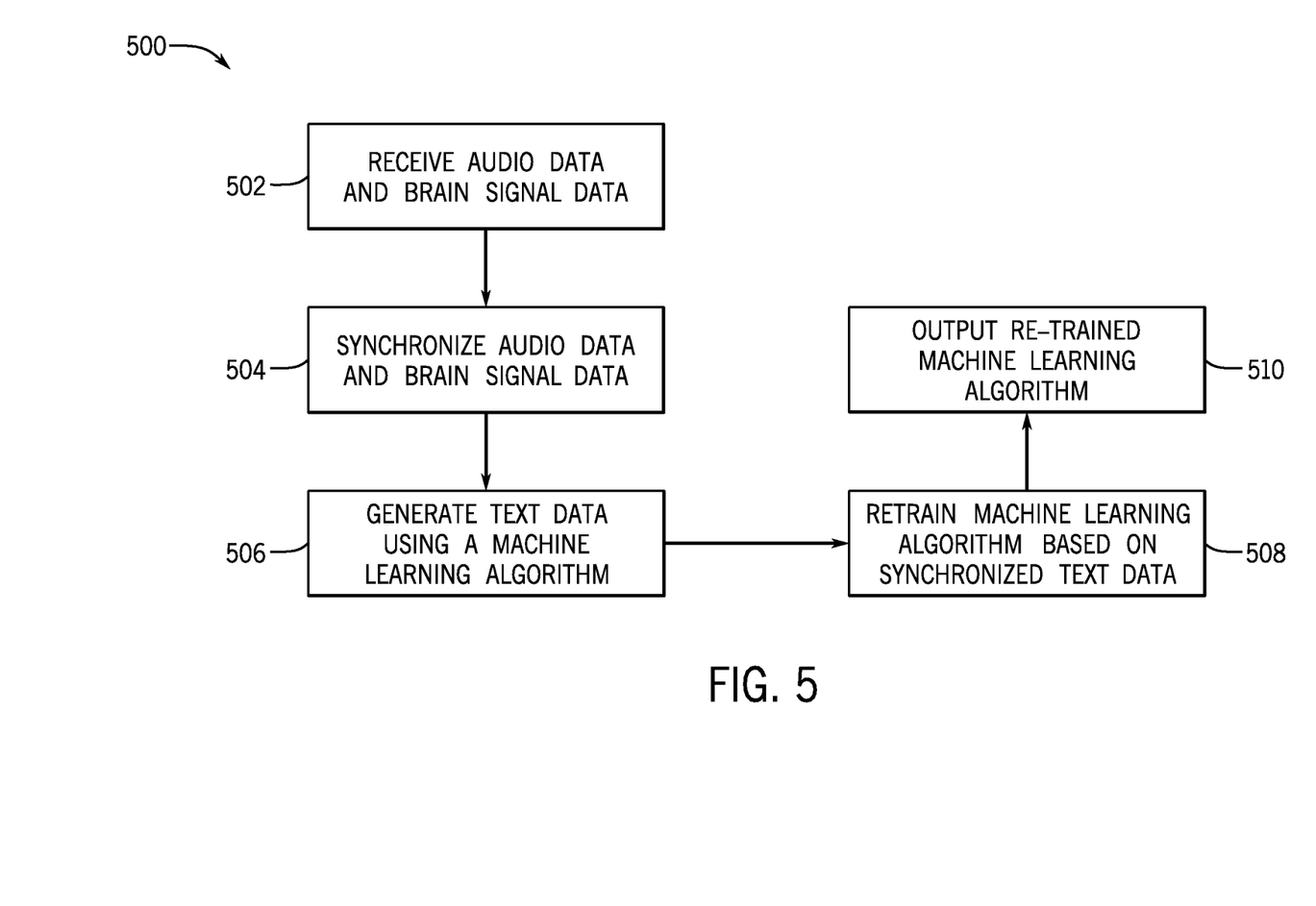
FIG. 5 is a flow diagram of a process for training the machine learning algorithm of FIG. 3, in accordance with an embodiment of the present disclosure.

With the preceding in mind, FIG. 5 is a flow diagram of a process 500 for training a machine learning algorithm, such as the machine learning algorithm 302 in FIG. 4, in accordance with an embodiment of the present disclosure. While the process 500 is described as being performed by the processor 110, it should be understood that the process 500 may be performed by any suitable device that may control and/or communicate with components of the non-auditory speech recognition system 100. Furthermore, while the process 500 is described using steps in a specific sequence, it should be understood that the present disclosure contemplates that the described steps may be performed in different sequences than the sequence illustrated, and certain described steps may be skipped or not performed altogether. In some embodiments, the process 500 may be implemented by executing instructions stored in a tangible, non-transitory, computer-readable medium, such as the memory 404, using any suitable processing circuitry, such as the processor 110.

In this process 500, the processor 110 receives (block 502) training data (e.g., audio data and brain signal data) as sensed and transmitted by, for example, the sensors 102, 112 of FIG. 1. In some embodiments, the audio data may be vibration data, a biometric signal, or any combination thereof and may include words spoken by a user 118. For example, the sensor 102 may be disposed on a user, such as user 118, and may detect vibrations in a nasal bone of the user. The processor 110 synchronizes (block 504) the audio data 202 and the brain signal data 116. For example, the processor 110 performs data processing steps, such as analyzing time stamps and time durations associated with each of the audio data and the brain signal data. As such, the processor 110 synchronizes the audio data 202 and the brain signal data 116 such that words spoken by the user 118 and/or heard by the user 118 (as represented by the audio data) match up with the same words being processed by the brain of the user 118 (as represented by the brain signal data).

The processor 110 generates (block 506) text data, such as the text data 308 in FIG. 3, based on the synchronized data and using a machine learning algorithm, such as machine learning algorithm 302. For example, the machine learning algorithm 302 compares extracted features associated with the audio data 202 and expected features and/or extracted features associated with training audio data, and generates sensed words based on the comparison. In certain embodiments, the generated text data 308 includes a text string corresponding to the same words sensed by the sensor 102.

The processor 110 inputs the synchronized data 206 and the generated text data 308 into the machine learning algorithm 302 to retrain the machine learning algorithm 302 (block 508). For example, the machine learning algorithm 302 extracts features from the brain signal data 116 and associates the extracted features with the generated text data 308. In certain embodiments, the machine learning algorithm 302 generates expected brain signal samples for any number of words and some of the expected brain signal samples corresponds to the generated text data 308. For example, the machine learning algorithm 302 compares expected brain signal samples with the input brain signal data 418 and determines that the input brain signal data 418 corresponds to words and/or phrases based on matches during the comparison. As such, the machine learning algorithm 302 compares the expected brain signal samples with input brain signal data 418 to determine and/or identify words processed by a brain of the user 118 (e.g., heard by the user 118 and/or processed before speaking). The processor 110 outputs the re-trained machine learning algorithm (block 510) based on the synchronized data # and the generated text data 308. Once re-trained, the processor 110 may receive input brain signal data 408 and input the input brain signal data 408 into the re-trained machine learning algorithm 302 to generate text data 418 based on the brain signal data 408.

Figure 6:
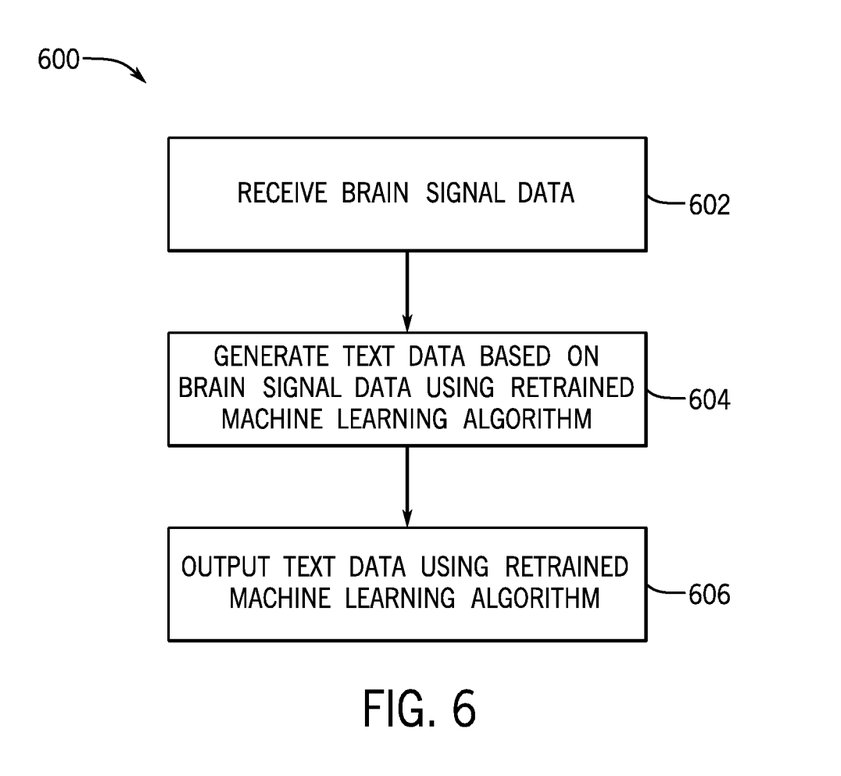
FIG. 6 is a flow diagram of a process for generating text data using the machine learning algorithm trained in FIG. 5, in accordance with an embodiment of the present disclosure.

With the preceding in mind, FIG. 6 is a flow diagram of a process 600 for process for generating text data, such as brain signal text data 418 in FIG. 4, using the re-trained machine learning algorithm 302 of FIG. 5, in accordance with an embodiment of the present disclosure. While the process 600 is described as being performed by the processor 110, it should be understood that the process 600 may be performed by any suitable device that may control and/or communicate with components of the non-auditory speech recognition system 100. Furthermore, while the process 600 is described using steps in a specific sequence, it should be understood that the present disclosure contemplates that the described steps may be performed in different sequences than the sequence illustrated, and certain described steps may be skipped or not performed altogether. In some embodiments, the process 600 may be implemented by executing instructions stored in a tangible, non-transitory, computer-readable medium, such as the memory 404, using any suitable processing circuitry, such as the processor 110.

In this process 600, the processor 110 receives (block 602) input brain signal data, such as the brain signal data 116, as sensed and transmitted by, for example, the sensor 112 of FIG. 1. For example, the sensor 112 senses electrical activity from a brain of the user 118. The processor 110 feeds the input brain signal data 418 into the re-trained machine learning algorithm 302 and generates (block 604) text data 418 based on the input brain signal data 408. For example, the processor 110 compares extracted features from the input brain signal data 408 with expected features associated with the re-trained machine learning algorithm 302. Each expected feature may correspond to a word or phrase and the processor 110 identifies text data 418 (e.g., words to be spoken or heard by the user) based on the comparison. As such, the processor 110 determines words and/or phrases that are spoken or were heard by the user 118 based on the comparison.

The processor 110 outputs (block 606) brain signal text data, such as the brain signal text data 418 in FIG. 4, using the re-trained machine learning algorithm 302. The brain signal text data 418 corresponds to a text string (e.g., words, phrases) processed by the brain of the user 118. For example, the user 118 hears the words, and the brain processes the words and generates associated electrical activity sensed by the sensor 112 that is then received by the processor 110 and used to generate the brain signal text data 418. Additionally or alternatively, the brain of the user 118 processes words and/or phrases to be spoken by the user 118. As such, the user 118 does not need to speak aloud to generate brain signal text data 418 when using the non-auditory speech recognition system 100. Advantageously, the processor 110 may generate the brain signal text data 418 based on the user 118 merely thinking the words, as speaking the words aloud is no longer necessary.

While the embodiments set forth in the present disclosure may be susceptible to various modifications and alternative forms, specific embodiments have been shown by way of example in the drawings and have been described in detail herein. However, it may be understood that the disclosure is not intended to be limited to the particular forms disclosed. The disclosure is to cover all modifications, equivalents, and alternatives falling within the spirit and scope of the disclosure as defined by the following appended claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

EXAMPLE EMBODIMENTS OF THE DISCLOSURE

The following numbered clauses define certain example embodiments of the present disclosure.

Clause 1.

A system, comprising:
a first sensor configured to sense brain signal data from a user, the brain signal data comprising nerve signals transmitted via a brain of the user and corresponding to a first set of words spoken by the user;
a second sensor configured to sense audio data from the user corresponding to the first set of words;
one or more processors communicatively coupled to the first sensor and the second sensor, the one or more processors configured to:
generate text data based on the audio data using a machine learning algorithm; and
re-train the machine learning algorithm based on the brain signal data and the text data to generate a re-trained machine learning algorithm, wherein the re-trained machine learning algorithm is configured to generate second text data associated with a second set of words based on second brain signal data.

Clause 2.

The system of clause 1, comprising a wearable device configured to be worn on a body part of the user, wherein the wearable device comprises the second sensor.

Clause 3.

The system of clause 1, wherein the first sensor is disposed on the brain of the user.

Clause 4.

The system of clause 1, comprising a brain-computer interface configured to receive the brain signal data from the first sensor and extract features associated with the brain signal data.

Clause 5.

The system of clause 4, wherein:
the brain-computer interface comprises the one or more processors; and
the one or more processors are disposed on a wearable device configured to be worn on a body part of the user.

Clause 6.

The system of clause 5, wherein the wearable device comprises a frame and wherein the second sensor is disposed on the frame.

Clause 7.

The system of clause 1, wherein:
the audio data comprises a first time stamp and the brain signal data comprises a second time stamp; and
the one or more processors are configured to synchronize the brain signal data and the audio data according to the first time stamp and the second time stamp.

Clause 8.

The system of clause 1, wherein the first sensor is configured to sense the brain signal data and the second sensor is configured to sense the audio data concurrently.

Clause 9.

A method, comprising:
receiving time-synchronized data comprising audio data and training brain signal data;
training a machine learning algorithm based on the time-synchronized data, wherein the machine learning algorithm is configured to generate text data based on brain signal data, wherein the brain signal data comprises electrical signals associated with the brain; and
receiving, from a sensor disposed on a brain of a user, the brain signal data, wherein the brain signal data corresponds to a set of words; and
generating, via the machine learning algorithm, the text data based on the brain signal data, wherein the text data corresponds to the set of words.

Clause 10.

The method of clause 9, comprising receiving, from the sensor, the training brain signal data, wherein the training brain signal data corresponds to a second set of words.

Clause 11.

The method of clause 10, comprising receiving, from a second sensor, the audio data, wherein the audio data corresponds to the second set of words.

Clause 12.

The method of clause 11, wherein the second sensor is a bone conduction microphone.

Clause 13.

The method of clause 9, wherein the time-synchronized data comprises a timestamp and a time duration associated with the audio data and the training brain signal data.

Clause 14.

The method of clause 13, comprising:
- comparing a first time stamp and a first sensing duration associated with the audio data and a second time stamp and a second sensing duration associated with the training brain signal data; and
- generating the time-synchronized data based on the comparison.

Clause 15.

A device, comprising:
- a sensor configured to sense brain signal data from a user, wherein the brain signal data comprises nerve signals transmitted via a brain of the user and the brain signal data corresponds to a first set of words;
- one or more processors communicatively coupled to the sensor and configured to:
  - receive time-synchronized data comprising audio data and training brain signal data, wherein the time-synchronized data corresponds to a second set of words;
  - generate training text data based on the time-synchronized data using speech recognition, wherein the training text data corresponds to the second set of words; and
  - train a machine learning algorithm based on the training brain signal data and the training text data, wherein the machine learning algorithm is configured to generate text data based on the brain signal data, wherein the text data comprises a text string corresponding to the first set of words; and
  - generate the text data based on the brain signal data.

Clause 16.

The device of clause 15, wherein the one or more processors are configured to:
- extract a first set of features associated with the audio data;
- compare the first set of features with a set of expected features corresponding the second set of words; and
- generate the training text data based on comparing the first set of features with the set of expected features.

Clause 17.

The device of clause 16, wherein the one or more processors are configured to:
- extract a second set of features associated with the training brain signal data; and
- associate the second set of features with the training text data, wherein a second set of expected features comprise the second set of features associated with the training brain signal data.

Clause 18.

The device of clause 17, wherein the one or more processors are configured to:
- extract a third set of features associated with the brain signal data;
- compare the third set of features with the second set of expected features; and
- generate the text data based on comparing the third set of features with the second set of expected features.

Clause 19.

The device of clause 15, wherein the time synchronized data comprises a time stamp and a time duration associated with the audio data and the training brain signal data and wherein the first set of words are spoken by the user.

Clause 20.

The device of clause 15, wherein the first set of words are spoken by a second user.

What is claimed is:

1. A system, comprising:
- a first sensor configured to sense brain signal data from a user, the brain signal data comprising nerve signals transmitted via a brain of the user and corresponding to a first set of words spoken by the user;
- a second sensor configured to sense audio data from the user corresponding to the first set of words;
- one or more processors communicatively coupled to the first sensor and the second sensor, the one or more processors configured to:
  - generate text data based on the audio data using a machine learning algorithm; and
  - re-train the machine learning algorithm based on the brain signal data and the text data to generate a re-trained machine learning algorithm, wherein the re-trained machine learning algorithm is configured to generate second text data associated with a second set of words based on second brain signal data.

2. The system of claim 1, comprising a wearable device configured to be worn on a body part of the user, wherein the wearable device comprises the second sensor.

3. The system of claim 1, wherein the first sensor is disposed on the brain of the user.

4. The system of claim 1, comprising a brain-computer interface configured to receive the brain signal data from the first sensor and extract features associated with the brain signal data.

5. The system of claim 4, wherein:
- the brain-computer interface comprises the one or more processors; and
- the one or more processors are disposed on a wearable device configured to be worn on a body part of the user.

6. The system of claim 5, wherein the wearable device comprises a frame and wherein the second sensor is disposed on the frame.

7. The system of claim 1, wherein:
- the audio data comprises a first time stamp and the brain signal data comprises a second time stamp; and
- the one or more processors are configured to synchronize the brain signal data and the audio data according to the first time stamp and the second time stamp.

8. The system of claim 1, wherein the first sensor is configured to sense the brain signal data and the second sensor is configured to sense the audio data concurrently.

9. A method, comprising:
- receiving audio data and training brain signal data;
- performing a comparison of a first time stamp and a first sensing duration associated with the audio data and a second time stamp and a second sensing duration associated with the training brain signal data;
- generating time-synchronized data based on the comparison;
- training a machine learning algorithm based on the time-synchronized data, wherein the machine learning algorithm is configured to generate text data based on brain signal data, wherein the brain signal data comprises electrical signals associated with the brain; and receiving, from a sensor disposed on a brain of a user, the brain signal data, wherein the brain signal data corresponds to a set of words; and generating, via the machine learning algorithm, the text data based on the brain signal data, wherein the text data corresponds to the set of words.

10. The method of claim 9, comprising receiving, from the sensor, the training brain signal data, wherein the training brain signal data corresponds to a second set of words.

11. The method of claim 10, comprising receiving, from a second sensor, the audio data, wherein the audio data corresponds to the second set of words.

12. The method of claim 11, wherein the second sensor is a bone conduction microphone.

13. The method of claim 9, wherein generating the time-synchronized data comprises synchronizing the audio data and the training brain signal data according to the first time stamp and the second time stamp.

14. The method of claim 13, wherein synchronizing the audio data and the training brain signal data comprises generating a time delay to compensate for a lag of the training brain signal data behind the audio data.

15. The method of claim 14, wherein synchronizing the audio data and the training brain signal data comprises applying the time delay to the audio data.

16. A device, comprising:
a sensor configured to sense brain signal data from a user, wherein the brain signal data comprises nerve signals transmitted via a brain of the user and the brain signal data corresponds to a first set of words;
one or more processors communicatively coupled to the sensor and configured to:
receive time-synchronized data comprising audio data and training brain signal data, wherein the time-synchronized data corresponds to a second set of words;
extract a first set of features associated with the audio data;
perform a comparison of the first set of features with a set of expected features corresponding to the second set of words;
generate training text data based on the comparison using speech recognition, wherein the training text data corresponds to the second set of words; and
train a machine learning algorithm based on the training brain signal data and the training text data, wherein the machine learning algorithm is configured to generate text data based on the brain signal data, wherein the text data comprises a text string corresponding to the first set of words; and
generate the text data based on the brain signal data.

17. The device of claim 16, wherein the one or more processors are configured to:
extract a second set of features associated with the training brain signal data; and
associate the second set of features with the training text data, wherein a second set of expected features comprise the second set of features associated with the training brain signal data.

18. The device of claim 17, wherein the one or more processors are configured to:
extract a third set of features associated with the brain signal data;
compare the third set of features with the second set of expected features; and
generate the text data based on comparing the third set of features with the second set of expected features.

19. The device of claim 16, wherein the time synchronized data comprises a time stamp and a time duration associated with the audio data and the training brain signal data and wherein the first set of words are spoken by the user.

20. The device of claim 16, wherein the first set of words are spoken by a second user.

* * * * *